United States Patent [19]

Aasen et al.

[11] Patent Number: 4,880,660

[45] Date of Patent: Nov. 14, 1989

[54] METHOD FOR PRIMING HARD TISSUE

[75] Inventors: Steven M. Aasen, Lakeland; Joel D. Oxman, St. Louis Park, both of Minn.

[73] Assignee: Minnesota Mining and Manufacturing Company, St. Paul, Minn.

[21] Appl. No.: 91,051

[22] Filed: Aug. 28, 1987

[51] Int. Cl.$^4$ .................... A61C 5/04; A61K 6/08; A01N 1/02; C09K 3/00

[52] U.S. Cl. .......................... 427/2; 106/35; 428/473; 433/226; 523/116

[58] Field of Search ................ 427/2; 428/473; 433/226; 523/116; 106/35

[56] References Cited

U.S. PATENT DOCUMENTS

| | | | |
|---|---|---|---|
| 3,954,475 | 5/1976 | Bonham et al. | 96/67 |
| 4,212,970 | 7/1980 | Iwasaki | 542/455 |
| 4,362,889 | 12/1982 | Bowen | 560/221 |
| 4,380,432 | 4/1983 | Orlowski et al. | 433/9 |
| 4,383,052 | 5/1983 | Higo et al. | 523/118 |
| 4,514,342 | 4/1985 | Billington et al. | 260/952 |
| 4,521,550 | 6/1985 | Bowen | 523/116 |
| 4,525,511 | 6/1985 | Kirby et al. | 524/158 |
| 4,533,701 | 8/1985 | Kusumoto et al. | 525/370 |
| 4,535,102 | 8/1985 | Kusumoto et al. | 523/116 |
| 4,538,990 | 9/1985 | Pashley | 433/217 |
| 4,539,382 | 9/1985 | Omura et al. | 526/276 |
| 4,553,941 | 11/1985 | Aasen | 433/228.1 |
| 4,593,054 | 6/1986 | Asmussen et al. | 523/118 |
| 4,645,456 | 2/1987 | James | 433/217.1 |
| 4,650,847 | 3/1987 | Omura et al. | 526/376 |
| 4,657,941 | 4/1987 | Blackwell et al. | 522/14 |
| 4,669,983 | 6/1987 | Bunker | 523/116 X |
| 4,677,140 | 6/1987 | Shiotsu | 523/116 |

FOREIGN PATENT DOCUMENTS 103420 3/1984 European Pat. Off. .

OTHER PUBLICATIONS

Patent Abstracts of Japan, vol. 10, No. 383 (C-393) (2440), Dec. 23, 1986, Citing JP-A-61 176507 (Kanebo Ltd.).

E. Asmussen and E. C. Munksgaard, "Adhesion of Restorative Resins to Dentinal Tissues", in Posterior Composite Resin Restorative Materials (G. Vanherle and D. C. Smith, Ed.), pp. 217–229 (Minnesota Mining and Manufacturing Co., 1985).

D. R. Beech, "Bonding of Restorative Resins to Dentin", id., at pp. 231–241.

R. L. Bowen, R. L. Blosser and A. D. Johnston, Abstract No. 915, p. 276, AIDR/AADR Abstracts 1985 (paper presented Mar. 22, 1985).

E. C. Munksgaard and E. Asmussen, *J. Dent. Res.*, 63, (8):1087–1089 (1984).

*Primary Examiner*—Michael Lusignan
*Attorney, Agent, or Firm*—Donald M. Sell; Walter N. Kirn; David R. Cleveland

[57] ABSTRACT

A single phase aqueous solution containing water, a water-soluble film former (e.g., 2-hydroxyethylacrylate) and a salt of an acid (e.g., calcium trifluoroacetate) is used as a primer for adhering to or overcoating hard tissue such as tooth dentin.

32 Claims, No Drawings

METHOD FOR PRIMING HARD TISSUE

CROSS-REFERENCE TO RELATED APPLICATION

This application is related to application Ser. No. 835,034, filed Feb. 28, 1986, now U.S. Pat. No. 4,719,149.

TECHNICAL FIELD

This invention relates to a method for priming hard tissue. This invention also relates to primer compositions for use on hard tissue.

BACKGROUND ART

In recent years there has been intense interest in the dental field in adhesives that bond to hard tissues such as dentin. Many of these adhesives have been used in conjunction with a pretreatment solution that is applied to the exposed dentin surface, allowed to stand for a short period of time, rinsed away and dried, followed by application of the adhesive. Many pretreatment solutions have been tried, with phosphoric acid, citric acid, oxalic acid and its salts, and various salts of ethylenediamine tetraacetic acid ("EDTA") being particularly popular pretreatments. The use of such pretreatment solutions, especially phosphoric acid, has not been without controversy. The American Dental Association has recommended against phosphoric acid pretreatment of dentin. However, phosphoric acid is extensively used as a pretreatment in Japan in conjunction with dentin adhesives from Kuraray Company, Ltd. Citric acid has a less severe etching effect than phosphoric acid and is used as a dentin pretreatment in the U.S. in conjunction with a dentin adhesive sold by Den-Mat Corporation. Oxalic acid also has a less severe etching effect than phosphoric acid, and the use of its monoacid or certain of its salts as a pretreatment is described in R. L. Bowen, R. L. Blosser, and A. D. Johnston, Abstract No. 915, p. 276, AIDR/AADR Abstracts 1985 (Paper presented March 22, 1985), and in U.S. Pat. Nos. 4,521,550 and 4,538,990. EDTA pretreatments are described in U.S. Pat. Nos. 4,553,941 and 4,593,054. Other references of interest include E. C. Munksgaard and E. Asmussen, *J. Dent. Res.*, 63, (8):1087–1089 (1984), E. Asmussen and E. C. Munksgaard, "Adhesion of restorative resins to dentinal tissues", in *Posterior Composite Resin Dental Restorative Materials* (G. Vanherle and D. C. Smith, Ed.) pp. 217–229 (Minnesota Mining and Manufacturing Co., 1985), D. R. Beech, "Bonding of restorative resins to dentin" id., at pp. 231–241, and U.S. Pat. Nos. 4,383,052, 4,514,342, and 4,645,456. The '342 and '456 patents discuss only adhesion to tooth enamel.

A reference of collateral interest to the instant invention, although not itself dealing with the priming of hard tissue, is U.S. Pat. No. 4,525,511. It describes an acid-containing primer for high solids enamel automotive finishes.

SUMMARY OF THE INVENTION

Typically in the above references a pretreatment solution is applied to hard tissue, allowed to stand, rinsed away with water, dried, and then overcoated with a dental adhesive composition. This sequence of steps is time-consuming, and the rinsing step is somewhat of a nuisance to both patient and practitioner. It would be desirable to reduce the time and simplify the steps required for completion of a bonding procedure.

In addition, it would be useful if a water-based polymerizable primer could be applied to hard tissues such as tooth dentin. That would substantially reduce the need to apply the primer in a dry field, thereby mediating the moist conditions present in the mouth.

The present invention provides, in one aspect, a method for adhering to or coating hard tissue, comprising the steps of:

(a) applying to said tissue a single phase aqueous primer solution comprising water, a water-soluble film former, and a salt of an acid, and (b) hardening said film former.

The present invention also provides a novel composition for use in such method. The composition (the "primer") is a single phase aqueous primer solution comprising said water, said film former and said salt, said solution being in the form of a film atop said hard tissue.

DETAILED DESCRIPTION

In the practice of the present invention, the hard tissues that can be adhered to or coated include human and animal tissues such as teeth (the component parts of which are enamel, dentin and cementum), bone, fingernails, and hoofs. The invention has particular utility for adhering to or coating dentin and enamel.

In a preferred method of the invention, the primer is permitted to stand on the hard tissue for a desired period of time, readily volatile cosolvents are removed therefrom (e.g., by air-drying) to leave a residual film on the surface of the hard tissue, the residual film is overcoated with a layer of additional film former (the additional film former can be water-soluble or water-insoluble but should form a homogeneous solution when combined with the residual film), then the additional film former and residual film are hardened and optionally overcoated with a composite or restorative (hereafter such composites and restoratives will be referred to collectively as "restoratives") or other hardenable coating. Thus the invention enables priming of hard tissue in order to improve the bond strength or durability of a restorative or coating applied thereto.

The primer is a single phase solution. By this is meant that the primer forms a homogeneous liquid and remains so when shaken briefly at room temperature and allowed to stand for a commercially practical period of time (e.g., a period of one half hour, the approximate duration of a typical dental appointment).

Preferably, the primer is free of any precipitated solids. However, the presence of minor amounts of precipitated solid salt apparently can be tolerated.

The water used in the primer of the invention preferably is substantially free of impurities that would be detrimental to storage stability, clinical acceptability and bond strength. Deionized or distilled water is preferred.

The film former is a water-soluble liquid substance or water-soluble liquid mixture of substances, such substance(s) being organic monomers, oligomers, or polymers, being different from the salt, and being capable of forming a hardenable (e.g., polymerizable) continuous or semicontinuous film on the surface of the hard tissue. As used herein, a "water-soluble" film former has a water solubility (exclusive of any water that may be present in the film former) of at least about 5 weight percent. Most preferably, the film former can be mixed with water in all proportions. Preferred film formers contain one or more substances having a sufficient number of water-solubilizing groups such as hydroxyl groups, carboxyl groups, sulfonic acid groups, cationic salts (e.g., ammonium, phosphonium or sulfonium groups), amide linkages or polyether linkages to render the film former water-soluble. The film former preferably wets the hard tissue and most preferably has a sufficiently low viscosity to enable it to flow into interstices in the surface of the tissue. To assist in hardening the film former, it preferably contains one or more polymerizable groups or ingredients. Addition polymerizable film formers (e.g., vinyl compounds such as acrylates and methacrylates) are especially preferred. The primer can also contain appropriate polymerization catalysts to assist in hardening the film former.

Preferred film formers include 2-hydroxyethylacrylate, 2-hydroxyethylmethacrylate ("HEMA"), 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl-1,2-diacrylate and dimethylacrylate, pentaerythritol diacrylate and dimethacrylate, acrylic acid, methacrylic acid, 2-trimethylammonium ethylmethacrylic chloride, 2-acrylamido-2-methylpropanesulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, polyethyleneglycol (400) diacrylate and dimethacrylate, and mixtures thereof.

The amount of film former in the primer should be sufficient to provide the desired degree of bonding strength, e.g., a bond strength on dentin of at least about 40 kg/cm$^2$, (more preferably at least about 80 kg/cm$^2$) when used in the procedure of EXAMPLE 1. The actual desired amount will vary somewhat depending upon the choice of salt and film former. As a general guide, the primer preferably contains about 10 to about 90 weight percent film former, more preferably about 25 to about 80 weight percent film former, and most preferably about 35 to about 70 weight percent film former.

The salt can be a salt of a mineral acid or an organic acid. For salts of organic acids, the acid can be monomeric, oligomeric or polymeric. Suitable salts of organic acids include salts of carboxylic acids, sulfonic acids, and phenols, with salts of alkylsulfonic acids and arylsulfonic acids being preferred, and salts of carboxylic acids being most preferred. The salt can have any suitable cation, e.g., an alkaline earth, alkali, transition metal or ammonium cation. The choice of cation will be affected in part by the anion employed. Alkaline earth salts, such as calcium salts and barium salts, and alkali salts, such as sodium and potassium salts, are preferred. Alkaline earth salts of organic acids (e.g, calcium haloacetate salts) are most preferred. Mixtures of salts can be used if desired.

The salt can be liquid or a solid; if a solid it preferably completely dissolves when added to the primer to enable the primer to form a single phase precipitate-free solution that will readily wet hard tissue.

The salt can in many cases be purchased commercially, or if desired can be prepared by salting an appropriate acid. The acid need not be completely neutralized; if desired a half salt or other partial salt can be used. Preferred inorganic acids from which the salt can be formed include HBr, HCl, and HNO. Preferred organic acids from which the salt can be formed include formic acid, trifluoroacetic acid, trichloroacetic acid, dichloroacetic acid, chloroacetic acid, tribromoacetic acid, dibromoacetic acid, bromoacetic acid, acetic acid, α-chloropropionic acid, propionic acid, maleic acid, fumaric acid, citraconic acid, pivalic acid, methacrylic acid, acrylic acid, trihydroxybenzoic acid, benzoic acid, camphorquinonesulfonic acid, camphorsulfonic acid, toluene sulfonic acid, trifluoromethanesulfonic acid, benzenesulfonic acid, 2-hydroxy-4-methoxybenzophenone-5-sulfonic acid, 2-acrylamido-2-methylpropane sulfonic acid, 2-naphthalene sulfonic acid, para-nitrophenol, 2,4-dinitrophenol, and phenol.

Sufficient salt should be present in the primer to provide the desired degree of bond strength. Preferably the salt has at least about 0.05 m (more preferably at least about 0.1 lm) solubility in the primer, where "m" stands for molality, or moles per 1000 grams of solution. A preferred amount of salt in the primer is between about 0.001 m and the limit of solubility, more preferably between about 0.01 m and about 1m, and most preferably between about 0.05 m and about 0.5 m.

The primer can also contain one or more suitable volatile cosolvents. The cosolvent(s) aid in wetting hard tissue and in solubilizing the film former or the salt. Suitable cosolvents include alcohols such as methanol, ethanol, 1-propanol, 2-propanol, and 2-methyl-2-propanol, ketones such as acetone and methyl ethyl ketone, aldehydes such as formaldehyde, acetaldehyde, propionaldehyde, acrolein, glutaraldehyde and 2-hydroxy-adipaldehyde, amides such as acetamide, and other organic solvents such as tetrahydrofuran and dimethyl sulfoxide. The film former preferably contains less than about 95 weight percent cosolvent, more preferably between 0 and about 50 weight percent cosolvent.

The primer can also contain adjuvants such as polymerization catalysts, fluoride compounds, indicators, dyes, wetting agents, buffering agents, thixotropes and the like, contingent upon attainment of the desired degree of bonding performance and suitability for use on the desired hard tissue.

Hard tissue to which the primer is applied preferably is first cleaned using conventional methods (e.g., by abrading it with a bur), rinsed (e.g., using water) and dried (e.g., using air). If desired, deep excavations in teeth can be lined with a conventional basing material (e.g., calcium hydroxide or a glass ionomer cement).

The primer should be allowed to stand on the surface of the hard tissue long enough to provide the desired degree of priming. The standing time will depend upon the particular salt and film former employed, the type of hard tissue and its intended use, and the time available for carrying out the priming procedure. Longer standing times tend to provide better priming. For priming dentin and enamel, standing times less than about 5 minutes, and preferably about 15 seconds to about one minute, provide very effective priming. Shorter or longer times can be used if desired.

As mentioned above, the primer preferably is overcoated with an optional layer of additional water-soluble or water-insoluble film former, and then hardened. Preferably, such additional film former is copolymerizable with the residual film formed by removal of volatile cosolvents from the primer, and contains a polymerization catalyst (preferably a photoinitiator) capable of hardening the residual film and additional film former upon exposure to light of a suitable wavelength. If desired, the additional film former can contain conventional fillers, and can also contain adjuvants of the type described above. A particularly preferred additional film former is obtained by combining the dimethacrylate derived from the reaction between methacrylic acid and the diglycidyl ether of bisphenol A ("Bis-GMA") with a hydrophilic monomer such as HEMA, hydroxypropyl methacrylate, or methacrylic acid, and a thixotrope such as fumed silica. Additional monomers that can be combined with Bis-GMA include tetrahydrofurfural methacrylate, glyceryl-1,3-dimethacrylate, triethyleneglycol dimethacrylate, ethyl methacrylate, n-hexyl methacrylate, polyethyleneglycol dimethacrylate, and 1,6-hexanediol dimethacrylate, urethane acrylates and methacrylates, and other monomers such as those contained in the adhesive compositions described in U.S. Pat. Nos. 4,650,847 and 4,657,941. The additional film former can also contain cosolvents of the type described above.

Polymerization catalysts that can be included in the primer or in the additional film former include autocure or light cure catalysts such as those mentioned in columns 28 and 29 of U.S. Pat. No. 4,539,382, chromophore-substituted halomethyl-s-triazines such as those shown in U.S. Pat. No. 3,954,475, and chromophore-substituted halomethyl-oxadiozoles such as those shown in U.S. Pat. No. 4,212,970.

As also mentioned above, the primer and optional additional film former preferably are overcoated with a conventional restorative or coating. The hard tissue can then be finished using conventional techniques. For example, on tooth tissue, the primer can be overcoated with a dental adhesive and dental restorative and used, for example, to restore teeth, to install crowns, bridgework or other prosthetic devices, to bond orthodontic brackets to enamel, to seal pits and fissures or to veneer dentin, cementum or enamel. On bone and hoofs, the primer can be used in conjunction with a conventional filled or unfilled bone cement (e.g., a methyl methacrylate-based cement) to repair fractures or to fill defects. On fingernails, the primer can be used in conjunction with a conventional polymerizable fingernail coating to strengthen a fingernail, alter its shape, color or smoothness or fasten an artificial fingernail thereto.

Adhesion to dentin of the primers of the invention was evaluated as follows:

Bovine teeth of similar age and appearance were partially potted in circular acrylic discs. The exposed portion of each tooth was ground flat and parallel to the acrylic disc using Grade 120 silicon carbide paper-backed abrasive mounted on a lapidary wheel, in order to expose the dentin. During this and subsequent grinding and polishing steps, the teeth were continuously rinsed with water. Further grinding and polishing of the teeth was carried out by mounting Grade 320 silicon carbide paper-backed abrasive and then Grade 600 silicon carbide paper-backed abrasive on the lapidary wheel. The polished teeth were stored in distilled water, and used for testing within 2 hours after polishing. The polished teeth were removed from the water and dried using a stream of compressed air. A single drop of primer composition (containing varying amounts of salt, film former and water) was painted onto each of the polished tooth surfaces with a brush and allowed to stand for 60 seconds. The primer was then blown dry with compressed air and overcoated with a layer of additional film former ("adhesive"). Unless otherwise indicated, the adhesive contained (by weight) 52.16% Bis-GMA, 42.62% HEMA, 4.5% fumed silica ("Cab-O-Sil M5", Cabot Corp.), 0.48% dimethylaminophenylethanol and 0.24% camphorquinone. The adhesive overcoat was applied with a brush and cured using a 20-second irradiation with a "Visilux 2" dental curing light. Previously prepared molds made from a 2- to 2.5-mm thick "Teflon" sheet with a 4- or 5-mm diameter hole through the sheet were clamped to each polished tooth so that the central axis of the hole in the mold was normal to the polished tooth surface. The hole in each mold was filled with a visible light-curable dental restorative (typically "Silux" brand restorative, universal shade, commercially available from 3M) and cured using a 20-second irradiation. The teeth and molds were allowed to stand for about 5 minutes at room temperature; then stored in distilled water at 37° C. for 24 hours (or shorter time if indicated). The molds were then carefully removed from the teeth, leaving a molded button of restorative attached to each tooth.

Adhesive strength was evaluated by mounting the acrylic disk in a holder clamped in the jaws of an "Instron" apparatus with the polished tooth surface oriented parallel to the direction of pull. A loop of orthodontic wire (0.44 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed, using a crosshead speed of 2 mm/min. The following examples are offered to aid in understanding of the present invention and are not to be construed as limiting the scope thereof. Unless otherwise indicated, all parts and percentages are by weight.

EXAMPLE 1

Using the procedure outlined above, the shear strength on dentin of primer compositions containing varying amounts of the salt calcium trichloroacetate was evaluated. The primers were made by dissolving the salt in a 60:40 mixture of HEMA and distilled water. Set out below in TABLE I are the run number, concentration of the salt in the primer, number of teeth tested and the average measured adhesive shear bond strength on dentin for each primer.

TABLE I

| Run | Concentration | No. of Teeth | Adhesion, kg/cm$^2$ |
| --- | --- | --- | --- |
| 1 | 0.00 m (control) | 10 | 67 |
| 2 | 0.01 m | 5 | 94 |
| 3 | 0.05 m | 5 | 145 |
| 4 | 0.10 m | 10 | 97 |
| 5 | 0.13 m | 10 | 182 |
| 6 | 0.20 m | 15 | 137 |
| 7 | 0.30 m | 15 | 152 |
| 8 | 0.40 m | 15 | 168 |

The above data illustrates that the presence of a salt in the primer provided an increase in adhesion to dentin.

EXAMPLE 2

Using the procedure of EXAMPLE 1, primers containing 0.2 m calcium trichloroacetate and varying amounts of HEMA and water were evaluated. Set out below in TABLE II are the run number, concentrations of HEMA and water in the primer, number of teeth tested, and the average measured shear bond strength on dentin for each primer.

TABLE II

| Run | Primer concentration, % | | No. of Teeth | Adhesion, kg/cm² |
| --- | --- | --- | --- | --- |
|  | HEMA | Water |  |  |
| 1 | 30 | 70 | 10 | 137 |
| 2 | 40 | 60 | 10 | 187 |
| 3 | 50 | 50 | 10 | 183 |
| 4 | 60 | 40 | 10 | 233 |
| 5 | 70 | 30 | 10 | 170 |
| 6 | 100 | 0 | 5 | 0 |

The above data illustrates that variation in the amounts of HEMA and water will affect dentin adhesion, and that both HEMA and water preferably are present.

EXAMPLE 3

Using the procedure of EXAMPLE 1, primers containing a variety of salts were evaluated. Set out below in TABLE III are the run number, salt, concentration of the salt in the primer, number of teeth tested, and the average measured adhesive shear bond strength on dentin for each primer.

TABLE III

| Run | Salt | Concentration | No. of teeth | Adhesion, kg/cm² |
| --- | --- | --- | --- | --- |
| 1 | NaCl | 0.1 m | 5 | 153 |
| 2 | LiF | 0.3 m | 10 | 24 |
| 3 | NaF | 0.3 m | 5 | 61 |
| 4 | NaF | 0.5 m | 3 | 39 |
| 5 | KF | 0.3 m | 5 | 0 |
| 6 | LiBr | 0.3 m | 5 | 5 |
| 7 | NaBr | 0.3 m | 5 | 80 |
| 8 | KBr | 0.3 m | 5 | 76 |
| 9 | Ca(Br)$_2$ | 0.3 m | 5 | 73 |
| 10 | NaNO$_3$ | 0.1 m | 4 | 84 |
| 11 | Ca(NO$_3$)$_2$ | 0.1 m | 6 | 161 |
| 12 | Ba(NO$_3$)$_2$ | 0.1 m | 4 | 72 |
| 13 | Zn(NO$_3$)$_2$ | 0.1 m | 3 | 53 |
| 14 | C$_6$H$_5$PO$_3$Ca | 0.1 m | 3 | 176 |
| 15 | CH$_3$COONa | 0.1 m | 5 | 159 |
| 16 | (CH$_3$COO)$_2$Ca | 0.1 m | 4 | 136 |
| 17 | ClCH$_2$COOLi | 0.1 m | 3 | 127 |
| 18 | ClCH$_2$COONa | 0.1 m | 3 | 172 |
| 19 | ClCH$_2$COOK | 0.1 m | 4 | 78 |
| 20 | (ClCH$_2$COO)$_2$Ca | 0.1 m | 3 | 103 |
| 21 | (ClCH$_2$COO)$_2$Ba | 0.1 m | 4 | 100 |
| 22 | (Cl$_2$CHCOO)$_2$Ca | 0.1 m | 9 | 173 |
| 23 | (Cl$_2$CHCOO)$_2$Ca | 0.17 m | 5 | 282 |
| 24 | (Cl$_3$COO)$_2$Ca | 0.05 m | 15 | 120 |
| 25 | (Cl$_3$COO)$_2$Ca | 0.1 m | 24 | 133 |
| 26 | (Cl$_3$COO)$_2$Ca | 0.2 m | 20 | 119 |
| 27 | (Cl$_3$COO)$_2$Ca | 0.3 m | 20 | 135 |
| 28 | (Cl$_3$COO)$_2$Ca | 0.4 m | 20 | 111 |
| 29 | (Br$_3$COO)$_2$Ca | 0.05 m | 10 | 152 |
| 30 | (Br$_3$COO)$_2$Ca | 0.2 m | 5 | 155 |
| 31 | (Br$_3$COO)$_2$Ca | 0.3 m | 5 | 150 |
| 32 | (H$_2$C=CHCOO)$_2$Ca | 0.1 m | 4 | 173 |
| 33 | (H$_2$C=CCH$_3$COO)$_2$Ca | 0.1 m | 5 | 119 |
| 34 | Calcium diglycolate | 0.1 m | 3 | 166 |
| 35 | Calcium maleate | 0.1 m | 8 | 82 |
| 36 | Sodium-4-acetylbenzene-sulfonate | 0.1 m | 3 | 112 |
| 37 | (C$_6$H$_5$O)hd 2Ca | 0.1 m | 4 | 106 |
| 38 | (m-BrC$_6$H$_4$COO)$_2$Ca | 0.1 m | 3 | 222 |
| 39 | (p-H$_3$C$_6$H$_4$SO$_3$)$_2$Ca | 0.3 m | 5 | 118 |
| 40 | Calcium camphor-10-sulfonate | 0.3 m | 9 | 190 |
| 41 | Calcium camphor-10-sulfonate | 0.2 m | 5 | 130 |
| 42 | Calcium camphor-10-sulfonate | 0.3 m | 5 | 131 |
| 43 | Calcium camphor-10-sulfonate | 0.4 m | 5 | 125 |
| 44 | Calcium camphorquinone-10-sulfonate | 0.3 m | 5 | 175 |
| 45 | None (control) | — | 50 | 106 |

The above data illustrates the use of a variety of salts. A higher average control value was obtained than was obtained for EXAMPLE 1. The source of this variation is unclear; it may have been due to variations in the test teeth, to the smaller sample size employed or to some other factor. In general, values tended to decrease over time. This is believed to have been caused by aging of the test teeth, which had been potted in acrylic early in the course of the study and then stored underwater until use.

Some of the observed values averaged less than the control. It is believed that in many cases a higher value could have been obtained by adjusting the amount of salt upward or downward. Primers containing salts of organic acids tended to have higher adhesion values than primers containing salts of inorganic acids.

Teeth bonded in accordance with Run 44 were, demineralized by immersion overnight in 50% nitric acid, then examined under a microscope to determine the topology of the tooth-primer interface. A relatively smooth and unblemished surface was observed, indicative of minimal dentin disturbance. In contrast a tooth primed as above, but using camphorquinone-10-sulfonic acid in place of the salt, would undergo substantial etching with concomitant formation of deep resin "tags" that would project into the dentin at the tooth-primer interface.

EXAMPLE 4

Using the procedure of EXAMPLE 1, 0.1 m portions of lactate salts with three different cations were dissolved in a primer containing a 40:60 HEMA:water mixture and evaluated for bond strength. Set out below in TABLE IV are the run number, cation, number of teeth and average measured shear bond strength on dentin for each primer.

TABLE IV

| Run | Cation | No. of teeth | Adhesion, Kg/cm² |
| --- | --- | --- | --- |
| 1 | K | 5 | 124 |
| 2 | Na | 5 | 91 |
| 3 | Ca | 5 | 39 |

EXAMPLE 5

Using the procedure of EXAMPLE 1, the average shear bond strength of a primer containing 0.3 m calcium trichloroacetate in a 60:40 HEMA:water mixture was evaluated at varying periods of time after bond formation. In a comparison run, "Light Cured Scotchbond Dental Adhesive" (3M) was used in place of the primer and adhesive, and its bond strength was evaluated immediately after bond formation. Set out below in TABLE V are the run number, time, number of teeth and average adhesive shear bond strength for each primer on dentin.

TABLE V

| Run | Time, min. | No. of teeth | Adhesion, kg/cm² |
| --- | --- | --- | --- |
| 1 | 0 | 5 | 87 |
| 2 | 15 | 5 | 99 |
| 3 | 30 | 5 | 104 |

TABLE V-continued

| Run | Time, min. | No. of teeth | Adhesion, kg/cm² |
|---|---|---|---|
| 4 | 60 | 5 | 78 |
| Comparison* | 0 | 5 | 20 |

*"Light Cured Scotchbond Dental Adhesive", 3M

The above data illustrates the rapid bond formation achieved by a primer of the invention. Rapid bond formation is desirable in order to discourage contraction gaps and microleakage, and to permit early finishing and polishing of a restoration.

EXAMPLE 6

Using the procedure of EXAMPLE 1, the primer of EXAMPLE 5, and "adhesives" containing Bis-GMA, the effect of using water-insoluble rather than water-soluble monomers in the adhesive was evaluated. Except where otherwise indicated, each adhesive contained 64.38% Bis-GMA, 34.37% monomer, 0.5% dimethylaminophenylethanol and 0.25% camphorquinone. Set out below in TABLE VI are the run number, adhesive monomer and the average measured shear bond strength on dentin.

TABLE VI

| Run | Adhesive monomer | Adhesion, kg/cm² |
|---|---|---|
| 1 | n-hexyl methacrylate | 20 |
| 2 | trimethylcyclohexyl methacrylate | 13 |
| 3 | triethyleneglycol dimethacrylate* | 33 |
| 4 | 2-hydroxyethyl methacrylate | 85 |

*Adhesive contained 49.63% Bis-GMA, 49.63% monomer, 0.5% dimethyaminophenylethanol and 0.25% camphorquinone.

The above data illustrates that an adhesive containing a water-soluble monomer (Run 4) provided higher adhesion than adhesives containing water-insoluble monomers (Runs 1-3).

Various modifications and alterations of this invention will be apparent to those skilled in the art without departing from the scope and spirit of this invention, and it should be understood that this invention is not limited to the illustrative embodiments set forth herein.

We claim:

1. A method for adhering to or coating hard tissue, comprising the steps of:
   (a) applying to said tissue a single phase aqueous primer solution comprising water, and effective amounts of a water-soluble film former and a salt of an acid, the amount of said water being sufficient so that said primer forms a homogeneous liquid when shaken briefly at room temperature, and
   (b) hardening said film former.

2. A method according to claim 1, wherein said film former contains one or more substances having a sufficient number of water-solubilizing groups to render said film former, exclusive of any water that may be present therein, soluble in water to at least about 5 weight percent, such water-solubilizing groups being selected from hydroxyl groups, carboxyl groups, sulfonic acid groups, cationic salts, amide linkages and polyether linkages.

3. A method according to claim 1, wherein said film former contains one or more addition-polymerizable substances having one or more hydroxyl groups, carboxyl groups or sulfonic acid groups.

4. A method according to claim 1, wherein said film former comprises 2-hydroxyethylmethacrylate.

5. A method according to claim 1, wherein said salt comprises a salt of a mineral acid.

6. A method according to claim 1, wherein said salt comprises a salt of an organic acid.

7. A method according to claim 6, wherein said salt comprises a salt of a carboxylic acid, alkylsulfonic acid, or arylsulfonic acid.

8. A method according to claim 1, wherein said salt has an alkaline earth or alkali cation.

9. A method according to claim 8, wherein said salt comprises a calcium salt.

10. A method according to claim 9, wherein said salt comprises a haloacetate salt.

11. A method for adhering to or coating hard tissue, comprising the steps of:
    (a) applying to said tissue a single phase aqueous primer solution comprising water, a water-soluble film former and a salt of an acid, and
    (b) hardening said film former, wherein said primer contains about 10 to about 90 weight percent of said film former, at least about 0.001 moles of said salt per 1,000 grams of said primer, and sufficient water so that said primer forms a homogeneous liquid when shaken briefly at room temperature.

12. A method for adhering to or coating hard tissue, comprising the steps of:
    (a) applying to said tissue a single phase aqueous primer solution comprising water, a water-soluble film former and a salt of an acid, and
    (b) hardening said film former, wherein said primer contains about 25 to about 80 percent of said film former, and about 0.01 to about 1 moles of said salt per 1000 grams of said primer, and sufficient water so that said primer forms a homogeneous liquid when shaken briefly at room temperature.

13. A method for adhering to or coating hard tissue, comprising the steps of:
    (a) applying to said tissue a single phase aqueous primer solution comprising water, a water-soluble film former and a salt of an acid, and
    (b) hardening said film former, wherein said primer contains about 35 to about 70 weight percent of said film former, about 0.05 to about 0.5 moles of said salt per 1000 grams of said primer, and sufficient water so that said primer forms a homogeneous liquid when shaken briefly at room temperature.

14. A method according to claim 1, wherein prior to hardening said film former, readily volatile solvents are removed therefrom to leave a residual film that is then overcoated with an additional film former that forms a homogeneous solution when combined with said residual film, said residual film and said additional film former being hardened using an autocuring or lightcuring polymerization catalyst.

15. A method according to claim 14, wherein said additional film former comprises a copolymerizable mixture of Bis-GMA and a hydrophilic monomer selected from the group consisting of 2-hydroxyethylmethacrylate, hydroxypropylmethacrylate and methacrylic acid, and said polymerization catalyst comprises a photoinitiator.

16. A primer composition, useful for adhering to or coating hard tissue, comprising a single phase aqueous solution comprising water, and effective amounts of a water-soluble film former and a salt of an acid, said solution being in the form of a film atop said hard tissue, the amount of said water being sufficient so that said primer forms a homogenous liquid hen shaken briefly at room temperature.

17. A composition according to claim 16, wherein said film former contains one or more substances having a sufficient number of water-solubilizing groups to render said film former, exclusive of any water that may be present therein, soluble in water to at least about 5 weight percent, such water-solubilizing groups being selected from hydroxyl groups, carboxyl groups, sulfonic acid groups, cationic salts, amide linkages and polyether linkages.

18. A composition according to claim 16, wherein said film former contains one or more addition-polymerizable substances having one or more hydroxyl groups, carboxyl groups or sulfonic acid groups.

19. A composition according to claim 16, wherein said film former comprises 2-hydroxyethylmethacrylate.

20. A composition according to claim 16, wherein said salt comprises a salt of a mineral acid.

21. A composition according to claim 16, wherein said salt comprises a salt of an organic acid.

22. A composition according to claim 21, wherein said salt comprises a salt of a carboxylic acid, alkylsulfonic acid, or arylsulfonic acid.

23. A composition according to claim 16, wherein said salt has an alkaline earth or alkali cation.

24. A composition according to claim 23, wherein said salt comprises a calcium salt.

25. A composition according to claim 24, wherein said salt is comprises a haloacetate salt.

26. A primer composition, useful for adhering to or coating hard tissue, comprising a single phase aqueous solution comprising water, water-soluble film former, and a salt of an acid, said solution being in the form of a film atop said hard tissue, wherein said solution contains about 10 to about 90 weight percent of said film former, at least about 0.001 moles of said salt per 1000 grams of said primer, and sufficient water so that said primer forms a homogeneous liquid when shaken briefly at room temperature.

27. A primer composition, useful for adhering to or coating hard tissue, comprising a single phase aqueous solution comprising water, water-soluble film former, and a salt of an acid, said solution being in the form of a film atop said hard tissue, wherein said solution contains about 25 to about 80 weight percent of said film former, about 0.01 to about 1 moles of said salt per 1000 grams of said primer, and sufficient water so that said primer forms a homogeneous liquid when shaken briefly at room temperature.

28. A primer composition, useful for adhering to or coating hard tissue, comprising a single phase aqueous solution comprising water, water-soluble film former, and a salt of an acid, said solution being in the form of a film atop said hard tissue, wherein said solution contains about 35 to about 70 weight percent of said film former, about 0.05 to about 0.5 moles of said salt per 000 grams of said primer, and sufficient water so that said primer forms a homogeneous liquid when shaken briefly at room temperature.

29. A method according to claim 1, wherein said solution contains polymerization catalyst.

30. A method according to claim 29, wherein said polymerization catalyst comprises light-cure catalyst.

31. A composition according to claim 16, wherein said solution contains polymerization catalyst.

32. A composition according to claim 31, wherein said polymerization catalyst comprises light-cure catalyst.

* * * * *

UNITED STATES PATENT AND TRADEMARK OFFICE
CERTIFICATE OF CORRECTION

PATENT NO. : 4,880,660
DATED : November 14, 1989
INVENTOR(S) : Steven M. Aasen & Joel D. Oxman It is certified that error appears in the above-identified patent and that said Letters Patent is hereby corrected as shown below:

Col. 4, line 2, "HNO:" should read --$HNO_3$.--.

Col. 6, line 33, "The following examples" should start a new paragraph.

Col. 6, line 67, "run number, ,concentrations" should read --run number, concentrations--.

Col. 12, line 23 (Claim 28), "000" should read --1000--.

Signed and Sealed this

Twenty-first Day of January, 1992

Attest:

HARRY F. MANBECK, JR.

*Attesting Officer*      *Commissioner of Patents and Trademarks*